United States Patent
Walker et al.

(10) Patent No.: US 11,278,420 B2
(45) Date of Patent: Mar. 22, 2022

(54) RECESSED POCKET SPINAL IMPLANT

(71) Applicant: Zavation, LLC, Flowood, MS (US)

(72) Inventors: John Lawrence Walker, Madison, MS (US); Colby Williams, Brandon, MS (US); Henry E. Aryan, Fresno, CA (US)

(73) Assignee: Zavation, LLC, Flowood, MS (US)

( * ) Notice: Subject to any disclaimer, the term of this patent is extended or adjusted under 35 U.S.C. 154(b) by 0 days.

(21) Appl. No.: 17/078,438

(22) Filed: Oct. 23, 2020

(65) Prior Publication Data

US 2021/0121298 A1    Apr. 29, 2021

Related U.S. Application Data

(60) Provisional application No. 62/925,873, filed on Oct. 25, 2019.

(51) Int. Cl.
| | |
|---|---|
| *A61F 2/44* | (2006.01) |
| *A61L 27/18* | (2006.01) |
| *A61L 27/06* | (2006.01) |
| *A61L 27/30* | (2006.01) |
| *A61F 2/28* | (2006.01) |
| *A61F 2/30* | (2006.01) |

(52) U.S. Cl.
CPC ............ *A61F 2/442* (2013.01); *A61F 2/2846* (2013.01); *A61F 2/30771* (2013.01); *A61L 27/06* (2013.01); *A61L 27/18* (2013.01); *A61L 27/306* (2013.01); *A61F 2/4455* (2013.01); *A61F 2002/3008* (2013.01); *A61F 2002/3093* (2013.01); *A61F 2002/30583* (2013.01); *A61F 2002/30827* (2013.01); *A61F 2310/00005* (2013.01); *A61F 2310/00023* (2013.01); *A61F 2310/00407* (2013.01); *A61L 2400/12* (2013.01); *A61L 2420/02* (2013.01); *A61L 2430/38* (2013.01)

(58) Field of Classification Search
CPC .... A61F 2/442; A61F 2/4455; A61F 2/30771; A61F 2002/30805; A61F 2002/3082; A61F 2002/30827; A61F 2002/30904; A61F 2002/30841; A61F 2002/30322; A61F 2310/00407; A61F 2002/3093
See application file for complete search history.

(56) References Cited

U.S. PATENT DOCUMENTS

| | | |
|---|---|---|
| 5,904,719 A | 5/1999 | Errico et al. |
| 6,371,986 B1 | 4/2002 | Bagby |
| 6,371,987 B1 | 4/2002 | Weiland et al. |
| 6,503,279 B1 | 1/2003 | Webb et al. |
| 6,565,606 B1 | 5/2003 | Bruce et al. |
| 6,638,310 B2 | 10/2003 | Lin et al. |
| 6,673,075 B2 | 1/2004 | Santilli |
| 7,056,577 B1 | 6/2006 | Bruce et al. |
| 7,225,713 B2 | 6/2007 | Apfel et al. |

(Continued)

*Primary Examiner* — Javier G Blanco
(74) *Attorney, Agent, or Firm* — IP & T Group LLP (57) ABSTRACT

A surgical implant and a surgical kit. The surgical implant having a body for contacting and supporting adjacent vertebrae. The body has a) opposing superior and inferior surfaces with or without corrugations, b) recesses formed in the opposing superior and inferior surfaces within a peripheral boundary of the body, and a recess-fill material (which preferably promotes osseointegration) disposed in the recesses.

7 Claims, 11 Drawing Sheets

(56) References Cited

U.S. PATENT DOCUMENTS

| | | |
|---|---|---|
| 7,553,539 B2 | 6/2009 | Bruce et al. |
| 8,221,503 B2 | 7/2012 | Garcia et al. |
| 8,414,651 B2 | 4/2013 | Tyber et al. |
| 8,480,715 B2 | 7/2013 | Gray |
| 8,814,939 B2 * | 8/2014 | Ullrich, Jr. ............ A61F 2/4465 623/17.16 |
| 9,226,992 B2 | 1/2016 | Mann et al. |
| 9,314,337 B2 | 4/2016 | Patterson et al. |
| 9,327,051 B2 | 5/2016 | Ullrich, Jr. et al. |
| 9,433,511 B2 * | 9/2016 | Bagga .................. A61F 2/4465 |
| 9,610,174 B2 | 4/2017 | Wang et al. |
| 9,700,431 B2 | 7/2017 | Nebosky et al. |
| 9,724,205 B2 | 8/2017 | Lin et al. |
| 9,730,802 B1 | 8/2017 | Harvey |
| 9,987,051 B2 | 6/2018 | Nunley et al. |
| 2003/0055505 A1 | 3/2003 | Sicotte et al. |
| 2004/0158327 A1 | 8/2004 | Bagby |
| 2006/0116766 A1 | 6/2006 | Lemaire |
| 2006/0173542 A1 | 8/2006 | Shikinami |
| 2008/0077248 A1 | 3/2008 | Murillo et al. |
| 2008/0154379 A1 | 6/2008 | Steiner et al. |
| 2009/0012620 A1 | 1/2009 | Youssef et al. |
| 2009/0187245 A1 | 7/2009 | Steiner et al. |
| 2012/0083882 A1 | 4/2012 | Shih et al. |
| 2013/0184827 A1 | 7/2013 | Lynn et al. |
| 2014/0142708 A1 | 5/2014 | Peterman et al. |
| 2016/0100954 A1 * | 4/2016 | Rumi .................... A61F 2/4611 623/17.16 |
| 2016/0213485 A1 | 7/2016 | Schaufler et al. |
| 2016/0228604 A1 | 8/2016 | Mann et al. |
| 2017/0312089 A1 * | 11/2017 | Duarte .................. A61F 2/4455 |
| 2018/0092754 A1 * | 4/2018 | Jang ...................... A61F 2/4455 |
| 2018/0256336 A1 * | 9/2018 | Mueller .................... A61F 2/30 |
| 2019/0053910 A1 * | 2/2019 | Sansur ...................... A61F 2/441 |

* cited by examiner

Background Art

RECESSED POCKET SPINAL IMPLANT

CROSS REFERENCE TO RELATED APPLICATIONS

This application is related to and claims priority to U.S. Ser. No. 62/925,873 entitled RECESSED POCKET SPINAL IMPLANT (the entire contents of which are incorporated herein by reference) filed Oct. 25, 2019.

BACKGROUND OF THE INVENTION

Field of the Invention

The present invention relates to implant devices for treating spinal disorders.

Description of the Related Art

Disorders of the spine often result in degeneration of the spinal disc in the intervertebral space between the vertebral bodies. Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-operative treatment requires patients to adjust their lifestyles and submit to pain relievers and a level of underlying pain. Operative treatment options include disc removal or insertion of devices or bone grafts to fixate or fuse vertebra together. Screw and rod systems, interbody spacers, threaded fusion cages, and the like could be used.

In the case of disc removal, the previously disc separated vertebral bodies can collapse or misalign. This can cause spinal instability, abnormal joint mechanics, arthritis, nerve damage, and severe pain. To prevent this, the removed disc is usually replaced with prosthetic spacers constructed from a biocompatible synthetic material or allograft bone. These spacers can become dislodged leading to severe complications. Pathways that permit or stimulate bone growth and allow adjacent vertebra to fuse together can help prevent this. Such bone growth helps ensure adequate implant retention and helps strengthen the vertebral joint. Moreover, mimicking the bone density of adjacent vertebra can help prevent implant rejection and non-union.

The following patent documents (which are incorporated herein by reference in their entirety) provide information as to the state of the art prior to this invention:
1. U.S. Pat. No. 6,565,606: entitled Implant, method of making the same and use the same;
2. U.S. Pat. No. 9,987,051: entitled Interbody spacer;
3. US 2009/0012620: entitled Implantable Cervical Fusion Device;
4. US 2014/0142708: entitled Spinal system and method including lateral approach;
5. US 2016/0213485: entitled Interbody spacer;
6. U.S. Pat. No. 5,904,719: entitled Interbody fusion device having partial circular section cross-sectional segments;
7. U.S. Pat. No. 6,371,986: entitled Spinal fusion device, bone joining implant, and vertebral fusion implant;
8. U.S. Pat. No. 6,371,987: entitled Device for connecting vertebrae of the vertebral column;
9. U.S. Pat. No. 6,503,279: entitled Intervertebral implant;
10. U.S. Pat. No. 6,638,310: entitled Intervertebral spacer and implant insertion instrumentation;
11. U.S. Pat. No. 6,673,075: entitled Porous intervertebral spacer;
12. U.S. Pat. No. 7,056,577: Body for providing ingrowth and growth of bone tissue and/or connective tissue and method of making such a body;
13. U.S. Pat. No. 7,225,713: entitled Cutting blade for a motor-driven, manually-guided implement;
14. U.S. Pat. No. 9,226,992: entitled Implantable cartilaginous tissue repair device;
15. U.S. Pat. No. 8,814,939: entitled Implants having three distinct surfaces;
16. U.S. Pat. No. 932,705: entitled Implants with integration surfaces having regular repeating surface patterns;
17. U.S. Pat. No. 9,610,174: entitled Intervertebral implant;
18. U.S. Pat. No. 9,700,431: entitled Orthopaedic implant with porous structure member;
19. U.S. Pat. No. 7,553,539: entitled Grain for providing cell growth;
20. U.S. Pat. No. 8,414,651: entitled Dynamic interbody;
21. U.S. Pat. No. 9,314,337: entitled Microstructured implant surfaces;
22. U.S. Pat. No. 9,724,205: entitled Biodegradable implant for intertransverse process fusion;
23. U.S. Pat. No. 9,433,511: entitled Interbody spinal implant having a roughened surface topography;
24. US 2003/0055505: entitled Intervertebral fusion device;
25. US 2004/0158327: entitled Bone joining implant with retaining tabs;
26. US 2006/0173542: entitled Biomaterial for artificial cartilage;
27. US 2006/0116766: entitled Anterior lumbar interbody implant;
28. US 2008/0077248: entitled Vertebral body replacement;
29. US 2008/0154379: entitled Interbody fusion hybrid graft;
30. US 2009/0187245: entitled Interbody fusion hybrid graft;
31. US 2012/0083882: entitled Spinal implant structure and method for manufacturing the same;
32. US 2016/0228604: entitled Method for the manufacture of an implantable cartilaginous tissue repair device;
33. US 2017/0312089: entitled Bone growth enhancing implant;
34. U.S. Pat. No. 8,221,503: entitled Spinal Implant;
35. U.S. Pat. No. 8,480,715: entitled Spinal Implant System and Method;
36. U.S. Pat. No. 9,730,802: entitled Spinal Fusion Implant and Related Methods; and
37. US 2013/0184827: entitled Spinal Implant.

Figure 1:
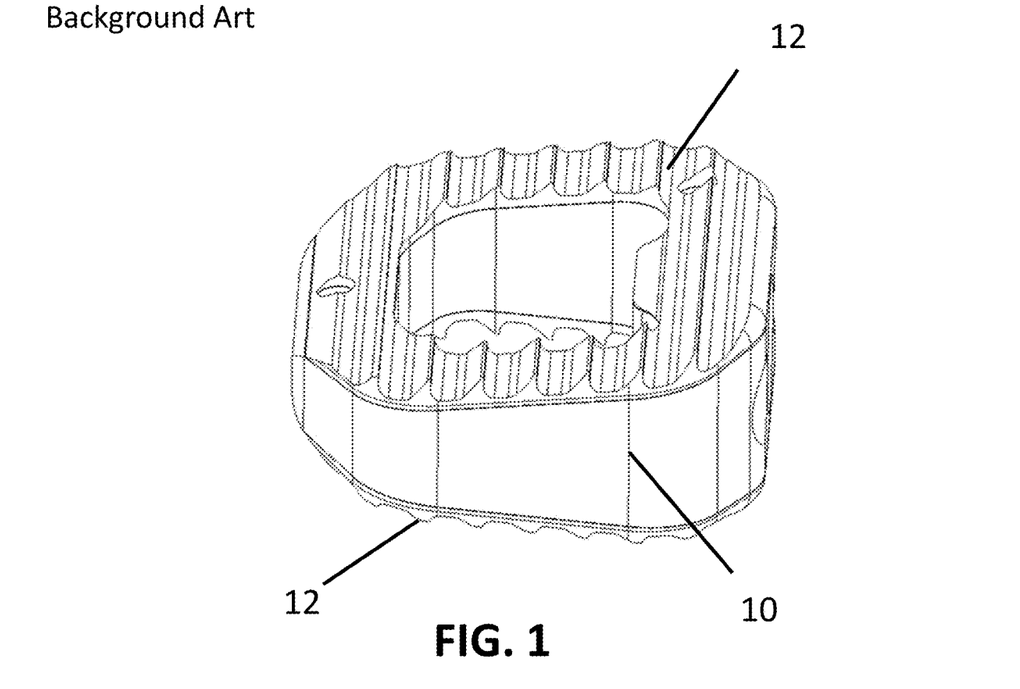
FIG. 1 is a schematic of a commercial implant having a titanium coating disposed over an entirety of the upper and lower faces.

Recently, as shown in FIG. 1, companies such as Aurora Spine (Carlsbad, Calif. 92008) have shown a PEEK implant 10 with titanium coatings 12 across the entire upper and lower faces of the PEEK implant.

SUMMARY OF THE INVENTION

In one embodiment, there is provided a surgical implant comprising a cage formed of PEEK for supporting adjacent vertebrae, the cage comprising opposing superior and inferior surfaces for contacting the adjacent vertebrae. The opposing superior and inferior surfaces have corrugations thereon for engaging the vertebrae. The surgical implant further has a peripheral portion of the cage surrounding at least one opening in the cage and extending between the superior and inferior surfaces to provide a graft window between the opposing superior and inferior surfaces. The peripheral portion includes at least some of the corrugations, and comprises a) a rim around an outside of the cage and b) a recess disposed interior to the rim and extending from the rim to the at least one opening. The surgical implant further has a titanium inlay disposed in the recess and filling the recess. The titanium inlay and the rim form the opposing superior and inferior surfaces having the corrugations for engaging the vertebrae.

In one embodiment, there is provided a surgical implant for supporting adjacent vertebrae, comprising: a body formed of a first material, the body comprising opposing superior and inferior surfaces for contacting the adjacent vertebrae; a peripheral portion of the body surrounding at least one opening in the body extending between the superior and inferior surfaces to provide a graft window. The superior surface comprises a first recess interior to the rim and extending from the rim to the at least one opening, and a first inlay in the first recess comprising a second material configured to promote osseointegration. The inferior surface comprises a second recess interior to the rim and extending from the rim to the at least one opening, and a second inlay in the second recess comprising the second material configured to promote osseointegration.

In one embodiment, there is provided a surgical implant comprising: a body for contacting and supporting adjacent vertebrae, the body having opposing superior and inferior surfaces with or without corrugations; first and second recesses formed respectively in the opposing superior and inferior surfaces within a peripheral boundary of the body, and a recess-fill material (which preferably promotes osseointegration) disposed in the first and second recesses, wherein first and second vertebrae-engaging surfaces of the recess-fill material in the first and second recesses are substantially level (within tolerances of the recess-fill material deposition process) with a topmost surface of the body and a bottommost surface of the body, respectively.

In one embodiment, there is provided a surgical implant comprising: a body for contacting and supporting adjacent vertebrae, the body having opposing superior and inferior surfaces with or without corrugations; first and second recesses formed respectively in the opposing superior and inferior surfaces within a peripheral boundary of the body, and a recess-fill material (which preferably promotes osseointegration) disposed in the first and second recesses. In this embodiment, an uppermost vertebrae-engaging surface of the recess-fill material in the first recess is lower than a topmost surface of the body, and a lowermost vertebrae-engaging surface of the recess-fill material in the second recess is above a bottommost surface of the body.

In one embodiment, there is provided a kit comprising: any one of the surgical implanted described above; and an intervertebral insertion device.

In one embodiment, there is provided a method for securing two bones surfaces together, comprising: providing between two bone surfaces the surgical implant of any of one of the above claims; supplying bone graft material into the surgical implant; and securing the surgical implant with the bone graft material in place between the two bone surfaces.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

The present invention addresses a problem of that surface titanium coatings on an implant can become dislodged due to the abrasive forces exerted when the implant is inserted between the vertebrae. To address this problem, in one embodiment of the invention (as shown in FIGS. 2-12), there is provided a surgical implant having a body 20 (or cage) for contacting and supporting adjacent vertebrae. The body 20 has opposing superior and inferior surfaces 22, 24 with or without corrugations 26. The body 20 has recesses 28 formed in the opposing superior and inferior surfaces within a peripheral boundary (or rim) 30 of the body 20. A recess-fill material 32 (which preferably promotes osseointegration such as titanium) is disposed in the recesses 28. At least one window 34 exists in the center of the body 20 extending from the superior surface 22 to the inferior surface 24. By having recesses in the superior and/or inferior surfaces 22, 24 (in which an osseointegration material such as the titanium is disposed), the titanium is protected from the abrasive forces exerted when the implant is inserted between the vertebrae.

The corrugations 26 if present may be corrugations 26$p$ on the peripheral boundary 30 and/or corrugations 26$r$ on the recesses 28. Corrugations 26$p$ and corrugations 26$r$ if present may be aligned or misaligned. Corrugations 26$p$ and corrugations 26$r$ may have the same height or different heights. Corrugations 26$p$ and corrugations 26$r$ if present may have the same pitch or different pitches. In one embodiment, the implant may only the corrugations 26*p* present on the rim or peripheral boundary 30.

Figure 2:
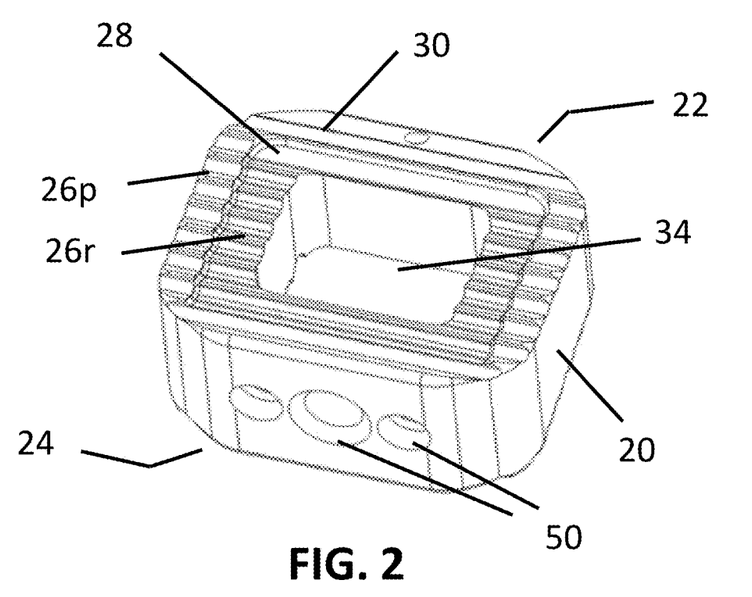
FIG. 2 is a schematic of an implant of the present invention having a recessed well configuration.

With respect to FIG. 2, the implant shown there has a rectangular body 20 with the recesses 28 formed inside and bounded by the peripheral boundary 30 of the body 20. In one embodiment, the sidewall(s) of body 20 may have apertures/openings 50 for coupling to an insertion tool used in the placement of the implant between the vertebrae. A bone graft material may be packed in the at least one window 34 prior to insertion of the implant between the vertebrae.

Figure 3:
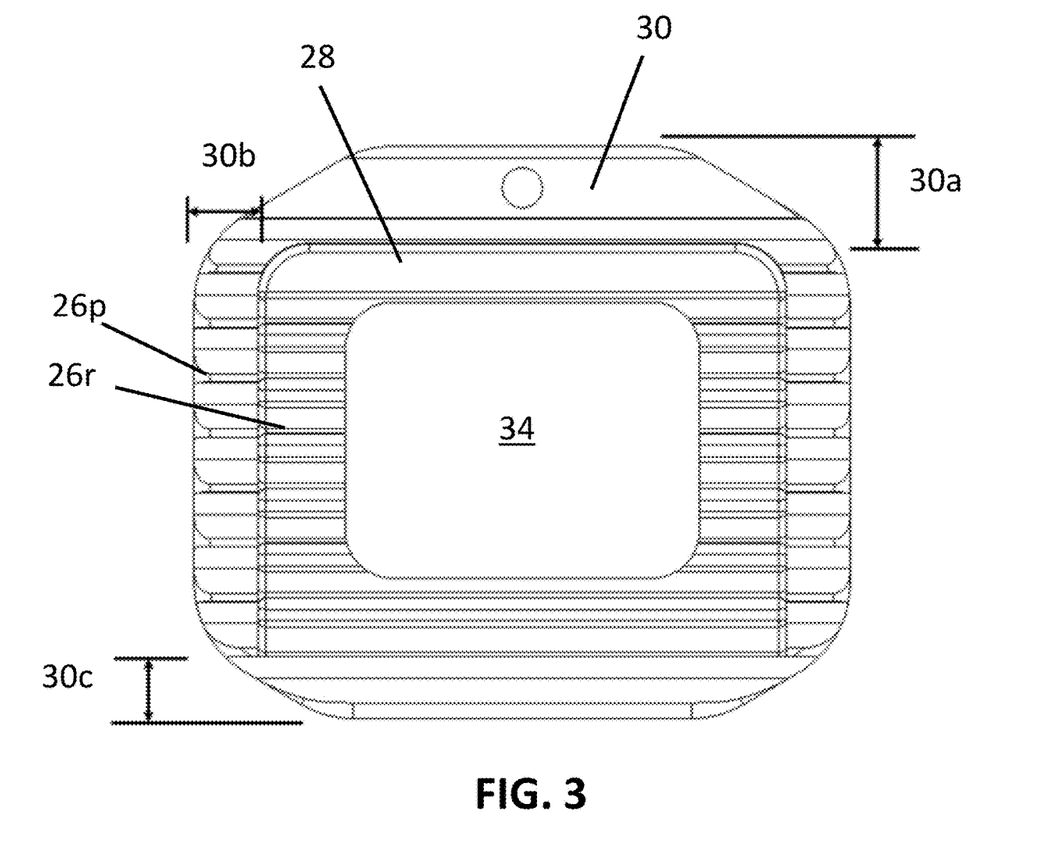
FIG. 3 is a schematic of a top view of the implant of FIG. 1.

FIG. 3 shows a top view of the implant of FIG. 2, and denotes thereon peripheral boundary regions 30*a*, 30*b*, and 30*c*. The interior edges of the peripheral boundary regions 30*a*, 30*b*, and 30*c* form an outer boundary for the recesses 28 on the opposing superior and inferior surfaces 22, 24. The window 34 forms the interior boundary for the recesses 28. In an illustrative embodiment, a width of peripheral boundary region 30*a* ranges from 1 mm to 10 mm, a width of peripheral boundary region 30*b* ranges from 0.5 mm to 5 mm, and a width of peripheral boundary region 30*c* ranges from 0.75 mm to 7.5 mm, although other dimensions are suitable in the present invention. In one embodiment, the peripheral boundary regions 30*a*, 30*b*, and 30*c* do not contain the osseointegration material. However, in other embodiments, an osseointegration material could be included on the corrugations 26*r* or in the valleys of the corrugations 26*p* on peripheral boundary 30. In one embodiment, the osseointegration material (such as titanium) or other recess-fill material 32 is plasma spray deposited onto the recesses 28. The osseointegration material may be commercially pure titanium, titanium alloys such as titanium-6 aluminium-4 vanadium or other metals such as zirconium. In one embodiment of the invention, the recess-fill material 32 has a thickness ranging from 25 to 500 microns, or from 50 to 300 microns, or from 75 to 250 microns.

Figure 4:
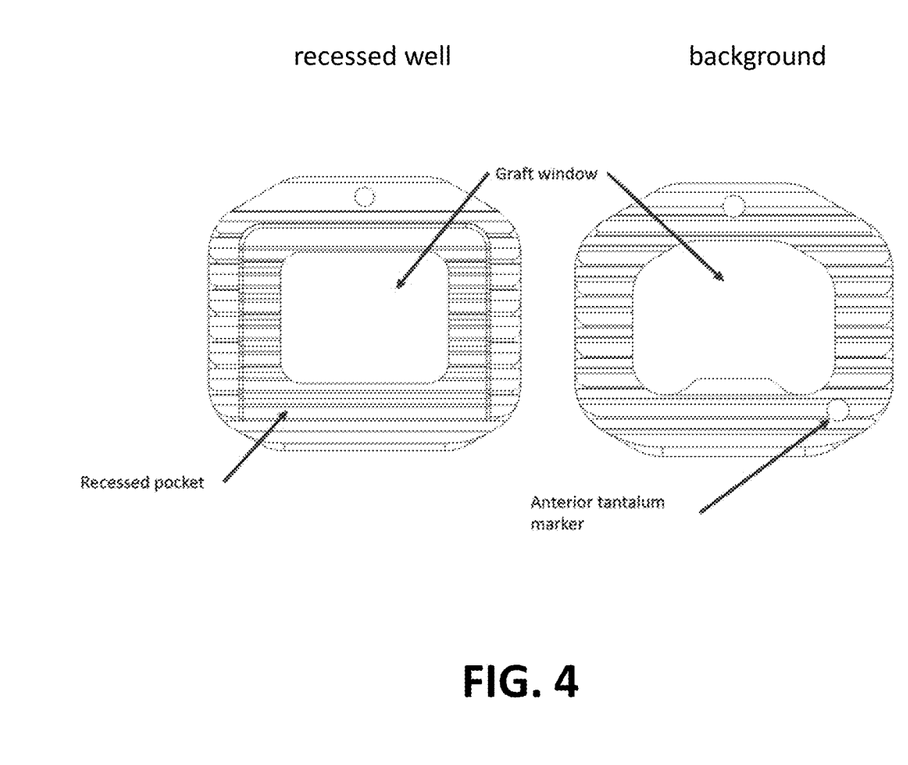
FIG. 4 is a schematic comparison of the implant of FIG. 1 to a background implant.

For the sake of clarity, FIG. 4 is a schematic comparing a conventional background implant to the implants of FIG. 2 having a recessed well configuration. In general, the implants of this invention with the recessed well configuration have recesses 28 formed inside the peripheral boundary 30, which (for a given implant outer dimension) results in a smaller graft window 34. Unlike the conventional background implant, anterior (or other specifically placed) radiographic markers are not needed for (but could be used with) the present inventive implants as the titanium (or other recess-fill material 32) serves as a radiographic marker.

In one aspect of the invention, as compared to an implant which may have all of its surfaces titanium coated, having the peripheral top area or rim free of titanium and having a titanium coating in the recess(es) of the implant of FIG. 1 helps prevent delamination of titanium and/or flaking of the titanium when the implants of the invention are inserted between vertebrae. By having the osseointegration material (such as titanium) in the recess(es) of the implant of FIG. 1, there is a confinement of the osseointegration material should it ever detach from the PEEK area when the implant is in place between vertebrae.

Figure 5:
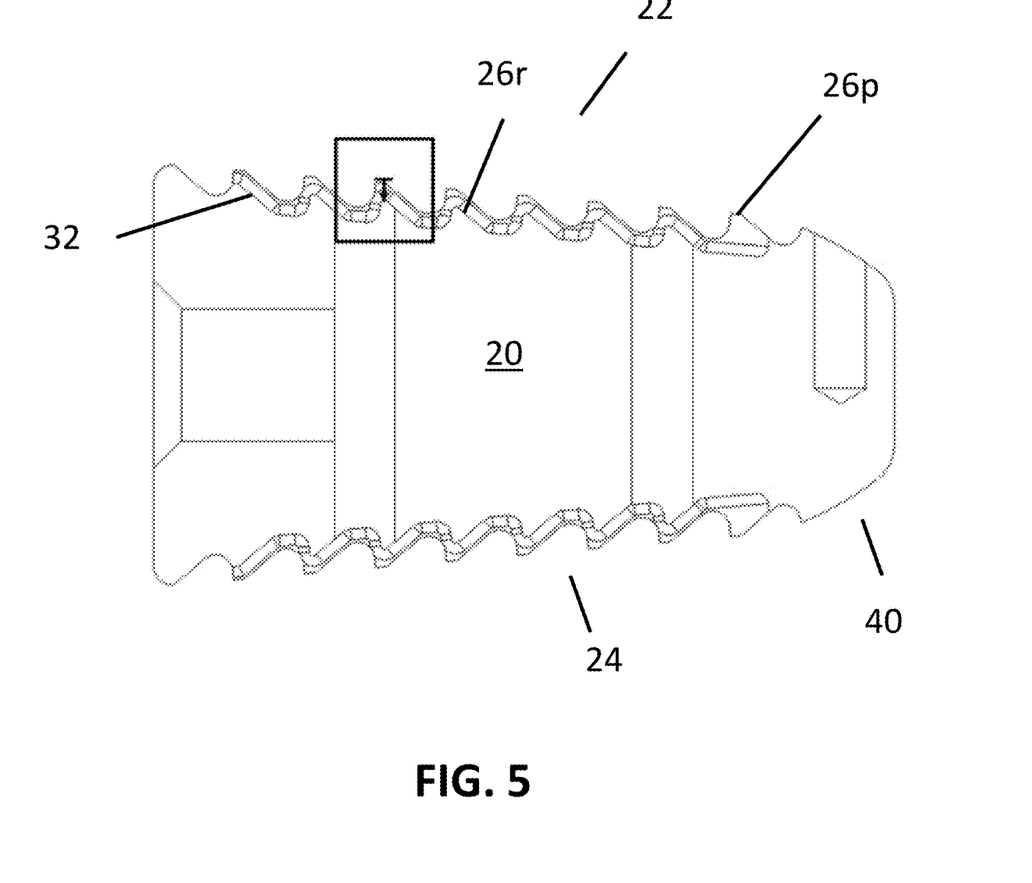
FIG. 5 is a schematic of a section of the implant of FIG. 1.
Figure 6:
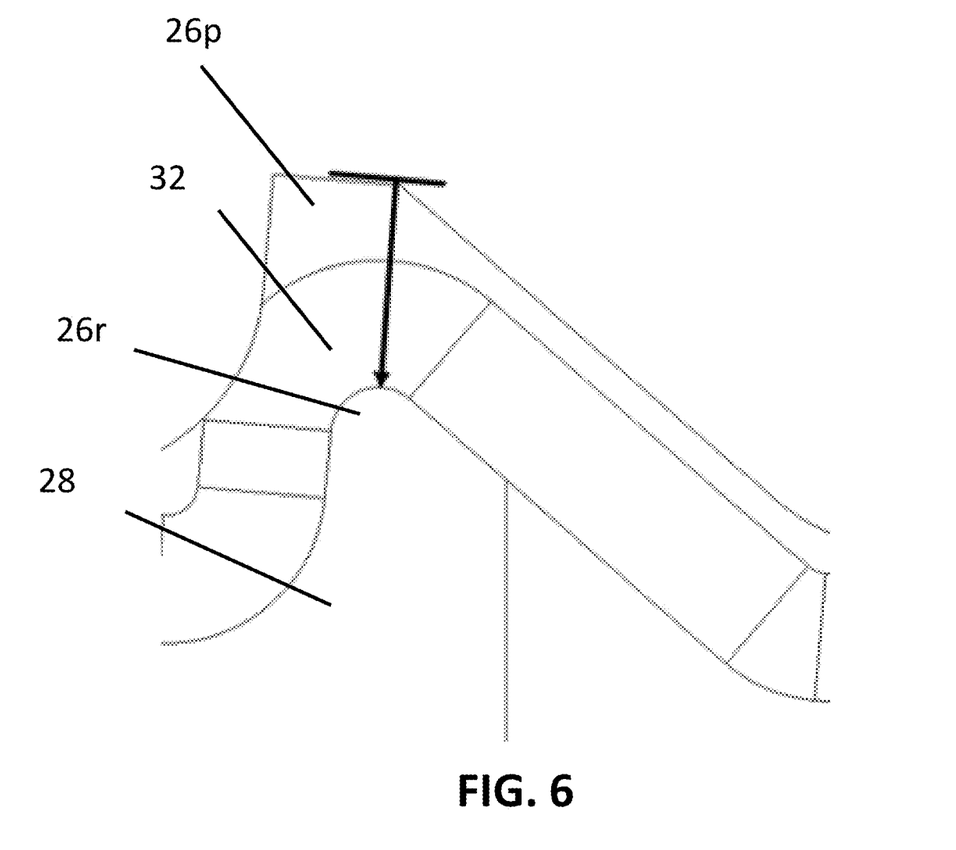
FIG. 6 is a schematic of an enlarged portion of the FIG. 5 schematic.

FIG. 5 is a schematic showing a view of the implant of FIG. 2 through a section of the recesses 28 and looking outwardly away from window 34. As illustrated in FIG. 5, the implant is tapered such that it has a greater thickness away the insertion end 40 that is to be inserted into the vertebrae. FIG. 6 is a schematic showing an enlarged view of a portion of FIG. 5. In one embodiment of this invention illustrated by FIGS. 5 and 6, the recess-fill material 32 fills the space above the recess but does not extend over the top of corrugations 26*p* on the peripheral boundary 30. In other words, the recess-fill material 32 fills the space above the recess but the top of the fills the space above the recess is below the top of the corrugations 26*p* on the peripheral boundary 30. In this way, the recess-fill material 32 is protected from the abrasive forces exerted when the implant is inserted between the vertebrae and is bounded (contained, trapped) after implantation between the peripheral boundary 30 of the body 20, the adjacent vertebra, and the base of the recess 28. In one embodiment of the invention, the recess-fill material 32 has a thickness ranging from 25 to 500 microns, and a vertical distance from the base of recess 28 to the top of protrusion 26*p* on the perimeter 30 is between 500 and 1000 microns. In one embodiment of the invention, the recess-fill material 32 has a thickness ranging from 50 to 300 microns, and a vertical distance from the base of recess 28 to the top of protrusion 26*p* on the perimeter 30 is between 300 and 800 microns. In one embodiment of the invention, the recess-fill material 32 has a thickness ranging from 75 to 250 microns, and a vertical distance from the base of recess 28 to the top of protrusion 26*p* on the perimeter 30 is between 250 and 500 microns.

Figure 7:
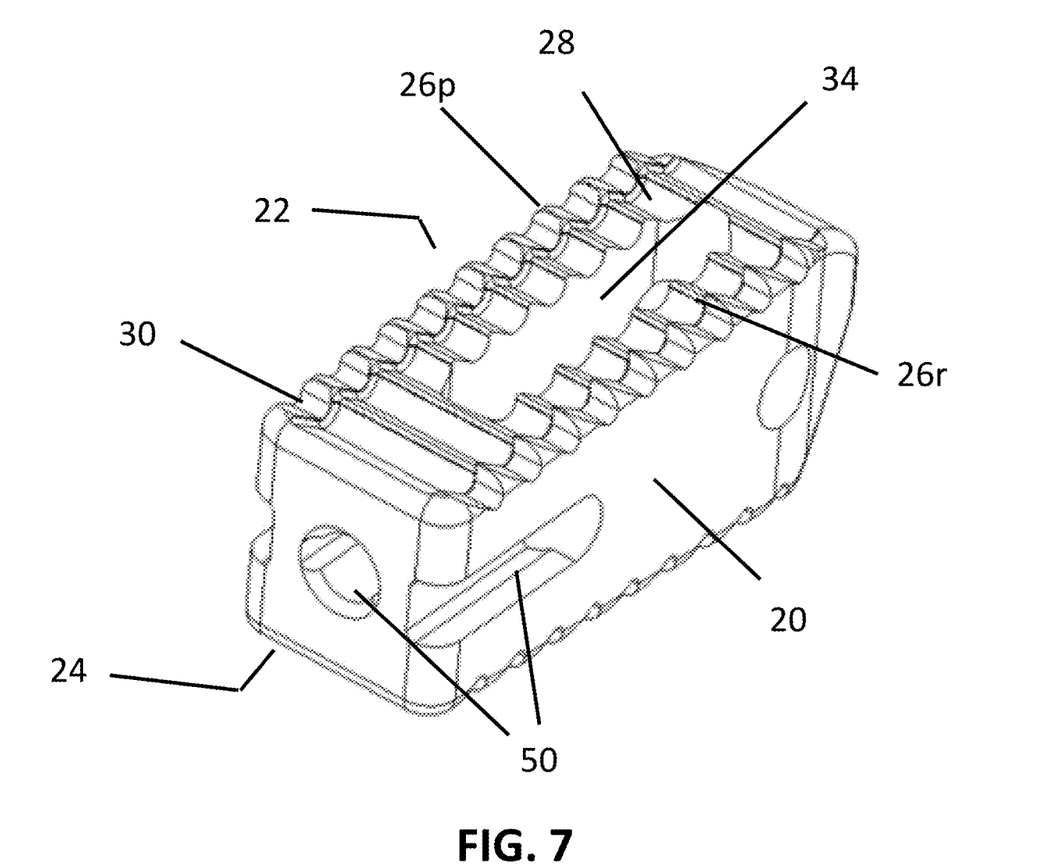
FIG. 7 is a schematic of another implant of the present invention having a recessed well configuration.

With respect to FIG. 7, the implant shown there has a more elongated body 20 that the implant of FIG. 2. Accordingly, in one embodiment of the invention, the graft window 34 is a rectangular opening extending form the superior surface 22 to the inferior surface 24. As with the implant of FIG. 2, window 34 forms the interior boundary for the recesses 28. As with the implant of FIG. 2, the osseointegration material (such as titanium) or other recess-fill material can be plasma spray deposited onto the recesses 28. As with the implant of FIG. 2, the recess-fill material can have a thickness ranging from 25 to 500 microns, or from 50 to 300 microns, or from 75 to 250 microns.

Figure 8:
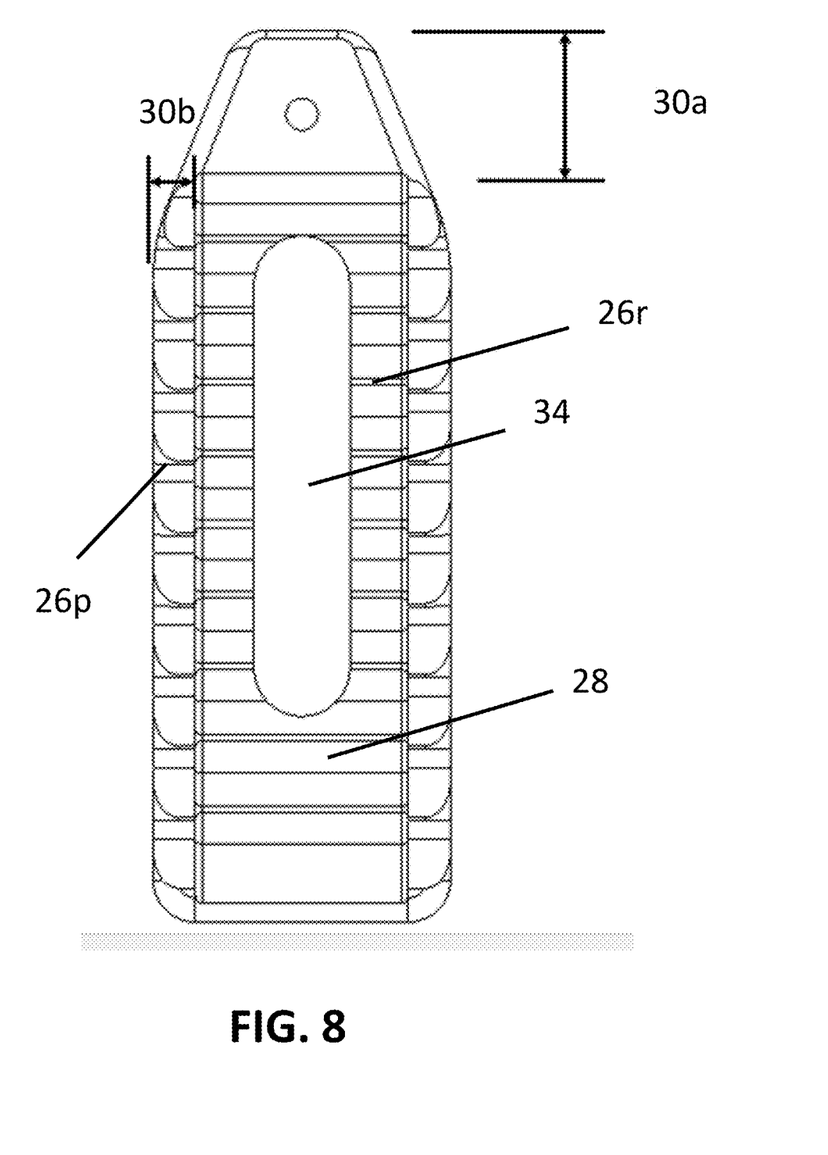
FIG. 8 is a schematic of a top view of the implant of FIG. 7.

FIG. 8 shows a top view of the implant of FIG. 7, and denotes thereon peripheral boundary regions 30*a* and 30*b*. The interior edges of the peripheral boundary regions 30*a* and 30*b* form an outer boundary for the recesses 28 on the opposing superior and inferior surfaces 22, 24. The recesses of the implant of FIG. 7 on the opposing superior and inferior surfaces 22, 24 extend all the way to the back of the implant where an insertion tool would connect. The window 34 forms the interior boundary for the recesses 28. In an illustrative embodiment, a width of peripheral boundary region 30*a* ranges from 2 mm to 15 mm, and a width of peripheral boundary region 30*b* ranges from 0.5 mm to 5 mm, although other dimensions are suitable in the present invention. In one embodiment, the peripheral boundary regions 30*a* and 30*b* do not contain the osseointegration material. However, in other embodiments, an osseointegration material could be included on the corrugations 26*r* or in the valleys of the corrugations 26*p* on peripheral boundary 30.

Figure 9:
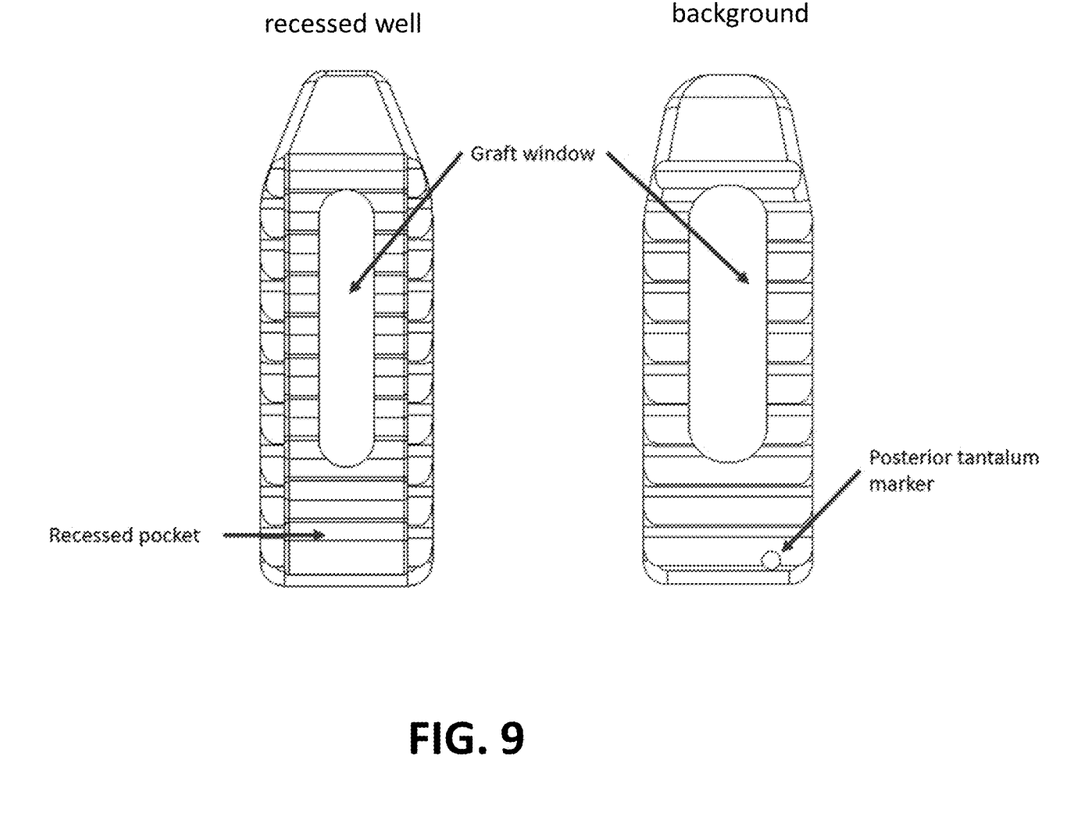
FIG. 9 is a schematic comparison of the implant of FIG. 7 to a background implant.

For the sake of clarity, FIG. 9 is a schematic comparing a conventional background implant to the implants of FIG. 7 having a recessed well configuration. The implants of FIG. 7 with the recessed well configuration has recesses 28 formed inside the peripheral boundary 30, which (for a given implant outer dimension) results in a smaller graft window 34. Unlike the conventional background implant, anterior (or other specifically placed) radiographic markers are not needed for (but could be used with) the implant of FIG. 7 as the titanium (or other recess-fill material 32) serves as a radiographic marker.

As with the implant of FIG. 2, for implant of FIG. 7, as compared to an implant which may have all of its PEEK surfaces titanium coated, having the peripheral top area free of titanium and a titanium coating in the recess(es) of the implant of FIG. 7 helps prevent delamination of titanium and/or flaking of the titanium the implants of the invention are inserted between vertebrae. By having the osseointegration material (such as titanium) in the recess(es) of the implant of FIG. 7, there is a confinement of the osseointegration material should it ever detach from the PEEK area when the implant is in place between vertebrae.

Figure 10:
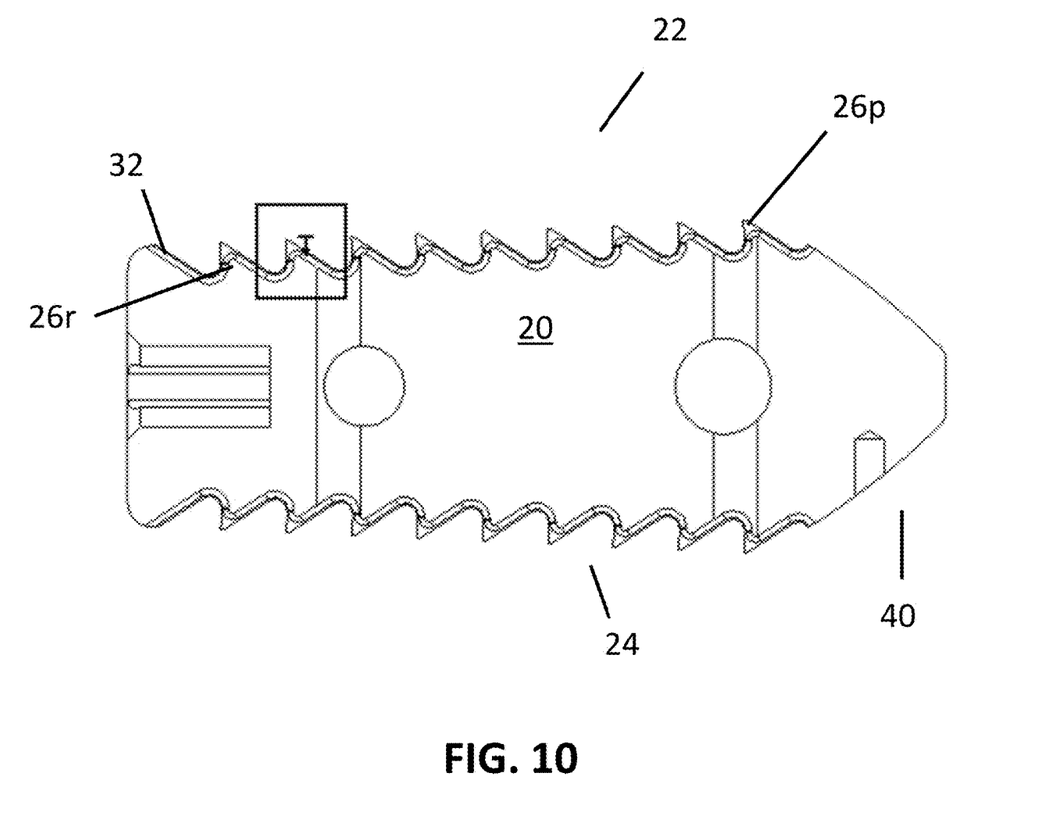
FIG. 10 is a schematic of a section of the implant of FIG. 7.
Figure 11:
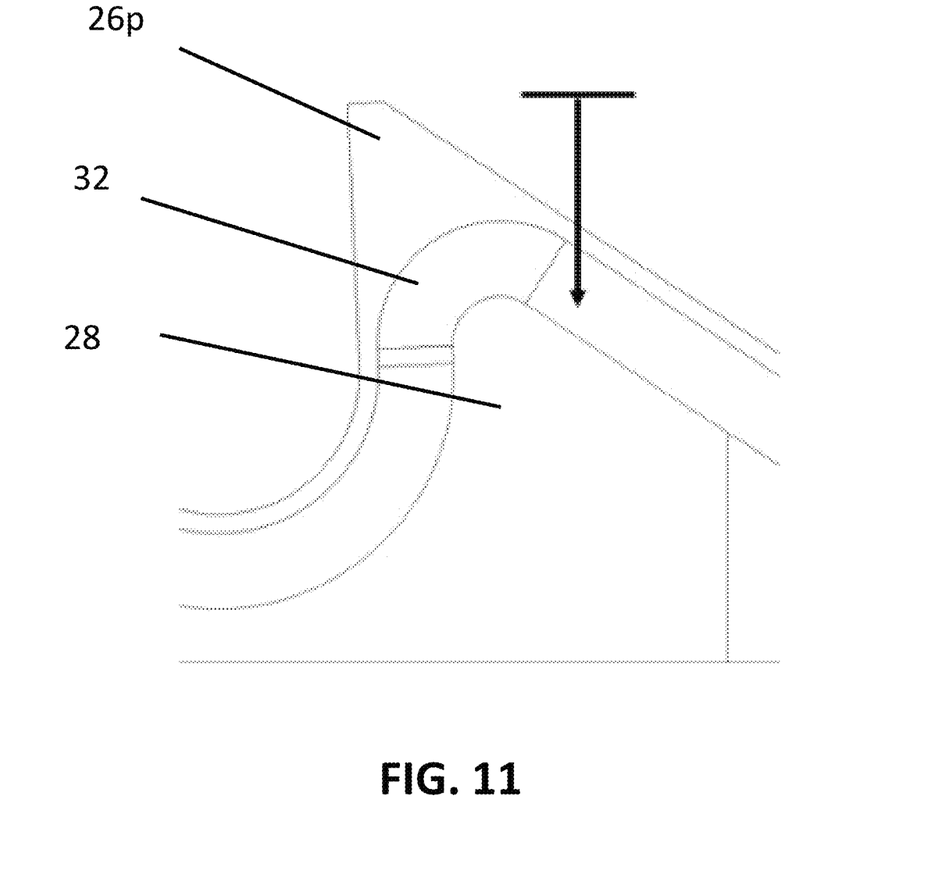
FIG. 11 is a schematic of an enlarged portion of the FIG. 10 schematic.

FIG. 10 is a schematic showing a view of the implant of FIG. 7 through a section of the recesses 28 and looking outwardly away from window 34. FIG. 11 is a schematic showing an enlarged view of a portion of FIG. 10. As illustrated in FIG. 10, the implant is tapered such that it has a greater thickness toward the insertion end 40 that is to be inserted into the vertebrae. In one embodiment of this invention illustrated by FIGS. 10 and 11, the recess-fill material 32 fills the space above the recess but does not extend over the top of corrugations 26p on the peripheral boundary 30. In other words, the recess-fill material 32 fills the space above the recess but the top of the fills the space above the recess is below the top of the corrugations 26p on the peripheral boundary 30. In this way, as with the implant of FIG. 2, the recess-fill material 32 is protected from the abrasive forces exerted when the implant is inserted between the vertebrae and is bounded (contained, trapped) after implantation between the peripheral boundary 30 of the body 20, the adjacent vertebra, and the base of the recess 28. As with the implant of FIG. 2, the recess-fill material 32 can have a thickness ranging from 25 to 500 microns, and a vertical distance from the base of recess 28 to the top of protrusion 26p on the perimeter 30 is between 500 and 1000 microns. As with the implant of FIG. 2, the recess-fill material 32 can have a thickness ranging from 50 to 300 microns, and a vertical distance from the base of recess 28 to the top of protrusion 26p on the perimeter 30 is between 300 and 800 microns. As with the implant of FIG. 2, the recess-fill material 32 can have a thickness ranging from 75 to 250 microns, and a vertical distance from the base of recess 28 to the top of protrusion 26p on the perimeter 30 is between 250 and 500 microns.

Figure 12:
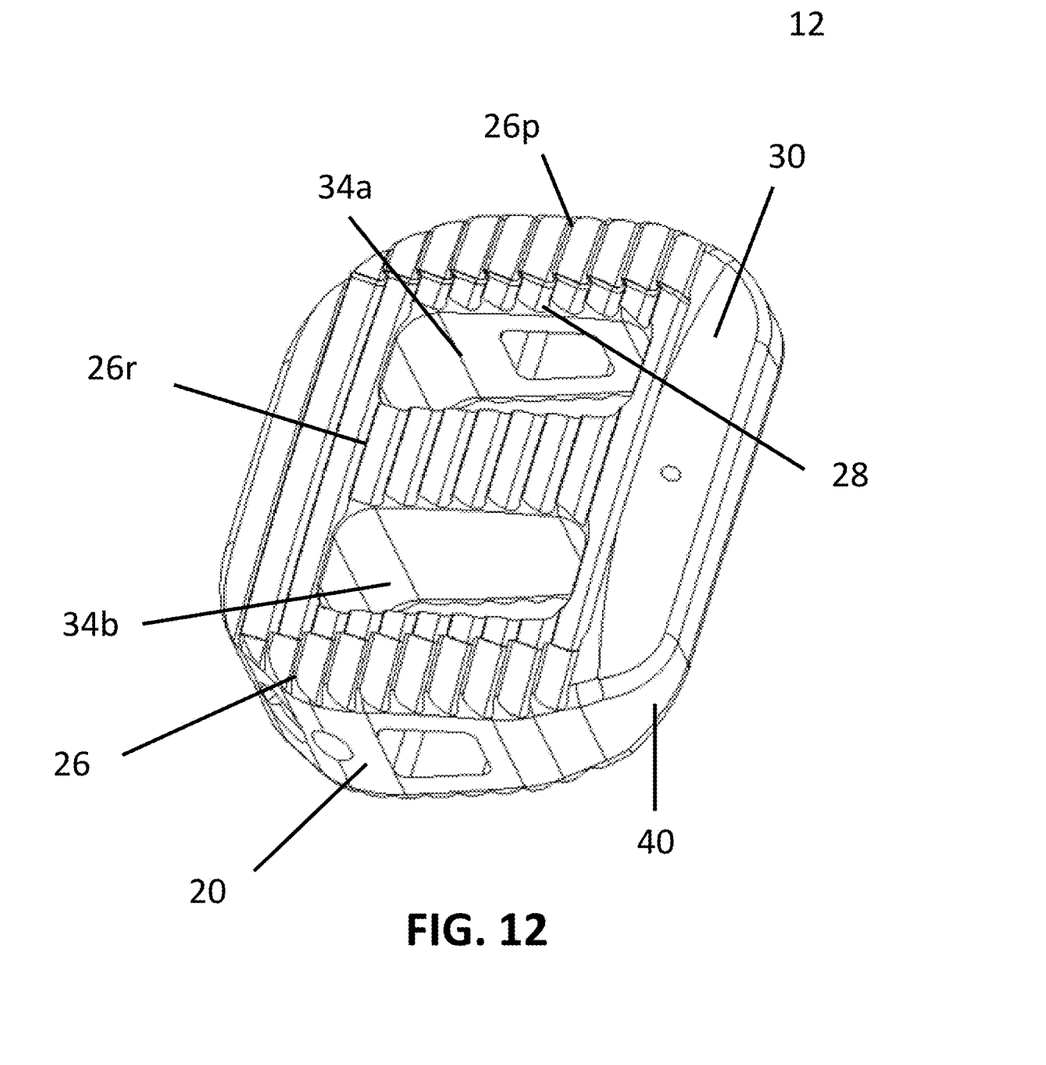
FIG. 12 is a schematic of another implant of the present invention having a recessed configuration.

FIG. 12 is a schematic illustration of another implant of the present invention. Many characteristics of the implant of FIG. 12 are similar to the implant of FIG. 2 and will be omitted here for the sake of brevity. Unlike implant of FIG. 2, the implant of FIG. 12 has two windows 34a and 34b that extend from a superior surface to an inferior surface. Unlike implant of FIG. 2, the recesses in the implant of FIG. 12 are like the recesses in the implant of FIG. 5 in that the recesses extend all the way to the end of the implant opposite the insertion end 40.

Accordingly, the implants of this invention are designed for improved spinal fusion procedures which promote bone growth and healing by having the osseointegration material be better preserved and held in place after implantation between vertebrae.

In one embodiment of this invention, commercially pure titanium (CP-Ti) coated PEEK cages are formed replicating the configurations shown in FIGS. 2-12.

Furthermore, in one aspect of the invention, the titanium in the recess(es) not only provides a radiographic marker that is quite coextensive with the length and width of the implant, but also (by the titanium not being on the sidewalls of PEEK body 20 and by the titanium not extending as a solid body across the height of the implant) permits a window for observing bone growth inside the PEEK cage(s) of the invention.

In one embodiment of the invention, the body of the implants (while shown above made of PEEK) may be formed of various metals such as for example cobalt chrome, stainless steel or titanium including its alloys, various plastics including those which are bio-absorbable, and may be formed of various ceramics or combinations of these materials, although preferably the body is made of medical grade PEEK (a polyetheretherketone which may comprise 5% to 75% carbon fibers by weight percent). The implants can have any regular geometrical shape (square, rectangular, circular) or any irregular shape, but preferably have the shapes shown in FIGS. 2-12.

In one embodiment, the implant includes a recess on the bone-bearing surface in which an inlay of titanium is deposited, preferably by a plasma spray process forming a nanograin titanium deposit. Although described with here with respect to commercially pure titanium, titanium alloys such as titanium-6 aluminium-4 vanadium or other metals such as zirconium may be used.

The implant can be of any size. An embodiment can be 5-12 mm high and have a lordotic angle of 0 or 5-10 degrees. Some embodiments could have footprints of 12 mm×14 mm, 13 mm×15 mm, or 14 mm×16 mm. Some embodiments will have degrees for the lordotic of 6 or 10 degrees.

In one embodiment of the invention, the implants can be packaged in a kit including an insertion device and/or a bone graft or autograft material. In general, a variety of bone graft materials are known and suitable for this invention. These typically include (but are not limited to) calcium phosphate-based or gel-based materials. Polymer-based bone graft substitutes containing (or not containing) collagen can be used. Ceramic bone graft substitutes can be used. In one embodiment, the implantable bone graft material comprises a composite of a ceramic and a polymer. The ceramic and the polymer can be present at a weight ratio ranging from about 10:1 ceramic to polymer to about 2:1 ceramic to polymer. Alternatively, the weight ratio of the ceramic to the polymer can range from about 2:1 (about 66% ceramic to about 33% polymer), from about 3:1 (about 75% ceramic to about 25% polymer), from about 4:1 (about 80% ceramic to about 20% polymer), from about 9:1 (about 90% ceramic to about 10% polymer), from about 10:1 (about 99% ceramic to about 1% polymer). Other bone graft materials besides those specifically listed above can be used.

This invention is also not limited to the methods by which the implants are made. The individual components can be machined from solid stock pieces. Molding can be used to make the individual components. In this case, machining to final dimensions may or may not be in order. The surfaces once properly dimensioned can be coated with a variety of biocompatible coatings and/or surface treatments. Various coatings include for example calcium phosphate ceramics, such as tricalcium phosphate (TCP) and hydroxyapatite (HA), and hydroxyapatite (a naturally occurring material in bone). Moreover, If the implant is not made of bone, surfaces of the implant that contact bone may be treated to promote fusion of the implant to the bone. Treatment may include, but is not limited to, applying a hydroxyapatite coating on contact surfaces, spraying a titanium plasma on contact surfaces, and/or texturing the contact surfaces by scoring, peening, implanting particles in the surfaces, or otherwise roughening the surfaces of the implant.

In some embodiments, any of the implants and instruments described above (such as the insertion tool) can be used with additional implants and instruments. In some embodiments, the implants and instruments can be used with stabilization members, such as plates, screws, and rods. In addition, a multi-level construct can be formed, wherein any one or more of the implants 20 described above can be used on one level, while a similar or different implant (e.g., fusion or prosthetic) can be used on a different level.

STATEMENTS OF THE INVENTION

The invention according to various embodiments can be characterized by the following generalized statements of the invention.

Statement 1. A surgical implant comprising: a cage formed of PEEK for supporting adjacent vertebrae, the cage comprising opposing superior and inferior surfaces for contacting the adjacent vertebrae; the opposing superior and inferior surfaces having corrugations thereon for engaging the vertebrae; a peripheral portion of the cage surrounding at least one opening in the cage and extending between the superior and inferior surfaces to provide a graft window between the opposing superior and inferior surfaces; the peripheral portion including at least some of the corrugations, and comprising:
 a) a rim around an outside of the cage, and
 b) a recess disposed interior to the rim and extending from the rim to the at least one opening; and
 a titanium inlay disposed in the recess and filling the recess such that the titanium inlay and the rim form the opposing superior and inferior surfaces having the corrugations for engaging the vertebrae.

Statement 2. The implant of statement 1, wherein the titanium inlay comprises a nano-grain titanium material, and preferably is disposed in the recess by plasma spraying the recess with a titanium coating.

Statement 3. The implant of statement 1, wherein the corrugations extend in a continuous section such that the corrugations on the rim are co-extensive with the corrugations on the inlay.

Statement 4. The implant of statement 1, wherein the inlay completely fills the recess such that a vertebrae-engaging surface of the titanium is substantially level (within tolerances of the titanium coating process) with a topmost or bottommost surface of the rim.

Statement 5. The implant of statement 1, wherein the inlay fills the recess such that the inlay is bound against a) delamination from the cage and b) translation out of the recess when the superior and inferior surfaces are engaging the vertebrae.

Statement 6. The implant of statement 1, wherein the titanium inlays comprises a radiographic marker.

Statement 7. The implant of statement 1, wherein the corrugations comprise asymmetric protrusions from the opposing surfaces.

Statement 8. The implant of statement 7, wherein the inlay follows a contour of the asymmetric protrusions.

Statement 9. The implant of statement m 1, where the cage comprises a distal tapered nose for sliding between the adjacent vertebrae.

Statement 10. The implant of statement 9, wherein a posterior end of the distal tapered nose adjoins to the corrugations such that a height of the distal tapered nose at the posterior end is substantially the same as total height of the cage.

Statement 11. A surgical implant for supporting adjacent vertebrae, comprising: a peripheral portion of the body surrounding at least one opening in the body extending between the superior and inferior surfaces to provide a graft window;
 the superior surface comprising,
  a first recess interior to the rim and extending from the rim to the at least one opening, and
  a first inlay in the first recess comprising a second material configured to promote osseointegration; and
 the inferior surface comprising,
  a second recess interior to the rim and extending from the rim to the at least one opening, and
  a second inlay in the second recess comprising the second material configured to promote osseointegration.

Statement 12. The implant of statement 11, further comprising a rim around an outside of the body,
 wherein the rim and the inlay comprise the opposing superior and inferior surfaces for contacting the adjacent vertebrae.

Statement 13. The implant of statement 12, wherein the rim and the inlay comprise corrugations for engaging the vertebrae.

Statement 14. The implant of statement 11, wherein the first material comprises PEEK.

Statement 15. The implant of statement 11, wherein the second material comprises titanium.

Statement 16. The implant of statement 11, wherein the second material comprises a titanium coating disposed on the first material.

Statement 17. The implant of statement 16, wherein the titanium coating comprises a nano-grain titanium material, and preferably is disposed in the recess by plasma spraying titanium onto the first and second recesses.

Statement 18. The implant of statement 11, wherein
 the first inlay fills the first recess such that the first inlay is bound against a) delamination from the body and b) translation out of the first recess when the superior and inferior surfaces are engaging the vertebrae, and
 the second inlay fills the second recess such that the second inlay is bound against a) delamination from the body and b) translation out of the second recess when the superior and inferior surfaces are engaging the vertebrae.

Statement 19. The implant of statement 11, wherein
 the first inlay completely fills the first recess such that a topmost vertebrae-engaging surface of the second material is substantially level (within tolerances of the second material deposition process) with a topmost surface of the rim, and
 the second inlay completely fills the second recess such that a bottommost vertebrae-engaging surface of the second material is substantially level (within tolerances of the second material deposition process) with a bottommost surface of the rim.

Statement 20. The implant of statement 11, wherein the second material in the first and second recesses comprises a radiographic marker.

Statement 21. The implant of statement 11, wherein no titanium exists within a predetermined distance of an anterior of the cage.

Statement 22. A surgical implant comprising:
 a body for contacting and supporting adjacent vertebrae, the body having opposing superior and inferior surfaces with or without corrugations;
 first and second recesses formed respectively in the opposing superior and inferior surfaces within a peripheral boundary of the body, and
 a recess-fill material (which preferably promotes osseointegration) disposed in the first and second recesses, wherein the recess-fill material in the first and second recesses is substantially level (within tolerances of the recess-fill material deposition process) with a topmost surface of the body and a bottommost surface of the body, respectively.

Statement 23. A surgical implant comprising:
a body for contacting and supporting adjacent vertebrae, the body having opposing superior and inferior surfaces with or without corrugations;
first and second recesses formed respectively in the opposing superior and inferior surfaces within a peripheral boundary of the body, and
a recess-fill material (which preferably promotes osseointegration) disposed in the first and second recesses,
wherein
an uppermost vertebrae-engaging surface of the recess-fill material in the first recess is lower than a topmost surface of the body, and
a lowermost vertebrae-engaging surface of the recess-fill material in the second recess is above a bottommost surface of the body.

Statement 24. The implant of statement 1 or statement 11 or statement 22 or statement 23, wherein a depth of the recess of statement 1, or a depth of the first recess or the second recess of statement 11, or a depth of the recesses of statement 22, or a depth of the recesses of statement 23 ranges from 5 to 10 mils or from 100 to 200 microns.

Statement 25. A kit comprising:
the surgical implant of any one of the above statements; and
an intervertebral insertion device.

Statement 26. A method for securing two bones surfaces together, comprising:
providing between two bone surfaces the surgical implant of any of one of the above statements;
supplying bone graft material into the surgical implant; and
securing the surgical implant with the bone graft material in place between the two bone surfaces.

Numerous modifications and variations of the present invention are possible in light of the above teachings. It is therefore to be understood that within the scope of the appended claims, the invention may be practiced otherwise than as specifically described herein.

The invention claimed is:

1. An intervertebral implant comprising:
a cage formed of PEEK for supporting adjacent vertebrae, the cage comprising opposing superior and inferior vertebrae-contacting surfaces for contacting the adjacent vertebrae;
the opposing superior and inferior vertebrae-contacting surfaces having corrugations thereon for engaging the vertebrae;
a peripheral portion of the cage surrounding at least one opening in the cage and extending between the superior and inferior vertebrae-contacting surfaces to provide a graft window between the opposing superior and inferior vertebrae-contacting surfaces;
the peripheral portion including at least some of the corrugations, and comprising a peripheral rim around an outside of the cage;
the superior surface comprising:
a first recess interior to the peripheral rim and extending from the peripheral rim to the at least one opening, the first recess having a shape complementary to the shape of the peripheral rim, and
a first titanium inlay disposed in the first recess and configured to promote osseointegration; and
the inferior surface comprising:
a second recess interior to the peripheral rim and extending from the peripheral rim to the at least one opening, the second recess having a shape complementary to the shape of the peripheral rim, and
a second titanium inlay disposed in the second recess and configured to promote osseointegration,
wherein the peripheral rim is devoid of titanium,
wherein the corrugations are present in both the peripheral rim and the first and second titanium inlays,
wherein:
the first titanium inlay fills the first recess such that a topmost vertebrae-engaging surface of the titanium is substantially level with a topmost surface of the peripheral rim, and
the second titanium inlay fills the second recess such that a bottommost vertebrae-engaging surface of the titanium is substantially level with a bottommost surface of the peripheral rim,
wherein:
the first titanium inlay fills the first recess such that the first titanium inlay is bound against a) delamination from the cage and b) translation out of the first recess when the superior vertebrae-contacting surface is engaging the vertebrae, and
the second titanium inlay fills the second recess such that the second titanium inlay is bound against a) delamination from the cage and b) translation out of the second recess when the inferior vertebrae-contacting surface is engaging the vertebrae.

2. The implant of claim 1, wherein the first and second titanium inlays comprise a nano-grain titanium material disposed by plasma spraying titanium onto the first and second recesses.

3. The implant of claim 1, wherein the corrugations on the peripheral rim are co-extensive with the corrugations on the inlays.

4. The implant of claim 1, wherein the corrugations comprise asymmetric protrusions protruding from the opposing vertebrae-engaging surfaces.

5. The implant of claim 1, where the cage comprises a distal tapered nose for sliding between the adjacent vertebrae.

6. The implant of claim 5, wherein a posterior end of the distal tapered nose adjoins to the corrugations such that a height of the distal tapered nose at the posterior end is substantially the same as total height of the cage.

7. The implant of claim 1, wherein a depth of the recesses ranges from 100 to 200 microns.

* * * * *